United States Patent [19]
Pozzetti

[11] 3,973,433
[45] Aug. 10, 1976

[54] METHOD AND RELATIVE APPARATUS FOR CONTROLLING THE CUTTING CAPACITY OF THE GRINDING WHEEL OF A GRINDER

[75] Inventor: Mario Pozzetti, Bologna, Italy

[73] Assignee: Finike Italiana Marposs-Soc. In Accomandita Semplice di Mario Possati & C., Bentivoglio, Italy

[22] Filed: Mar. 14, 1975

[21] Appl. No.: 558,439

Related U.S. Application Data

[62] Division of Ser. No. 365,734, May 31, 1973, Pat. No. 3,895,526.

[30] Foreign Application Priority Data
June 15, 1972 Italy.................................. 3459/72

[52] U.S. Cl................................ 73/104; 51/165.88
[51] Int. Cl.².......................................... G01N 3/56
[58] Field of Search........ 51/165 R, 165.88, 165.87; 73/104, 7, 9, 78

[56] References Cited
UNITED STATES PATENTS

| | | | |
|---|---|---|---|
| 3,500,811 | 3/1970 | Perkins.............................. 73/78 X |
| 3,641,713 | 2/1972 | Humes............................ 51/165.88 |
| 3,728,826 | 4/1973 | Nishimura....................... 51/165.88 |
| 3,760,539 | 9/1973 | Robillard........................... 51/165 R |
| 3,809,870 | 5/1974 | Auble et al............................ 73/104 |

FOREIGN PATENTS OR APPLICATIONS
1,289,452  10/1969  Germany........................ 51/165.87

*Primary Examiner*—Harold D. Whitehead
*Attorney, Agent, or Firm*—Stevens, Davis, Miller & Mosher

[57] ABSTRACT

Apparatus for checking the cutting capacity and controlling the dressing of a grinding wheel comprising a device to measure the sizes of the pieces being machined, a threshold unit connected to the output of the device responsive to the device, a processing group containing an integrating and memory circuit to integrate and store signals for every piece being machined, a switch associated with the integrating and memory circuit and controlled by the threshold unit, a threshold circuit the input of which is connected to the switch and the output to the processing group and a threshold device to control dressing of the grinding wheel connected to the output of the processing group. The apparatus may include a program unit to set the values of the feed speed of the wheelhead, a unit to calculate stock removal speed and a unit to compare stock removal speed with programmed speed.

7 Claims, 5 Drawing Figures

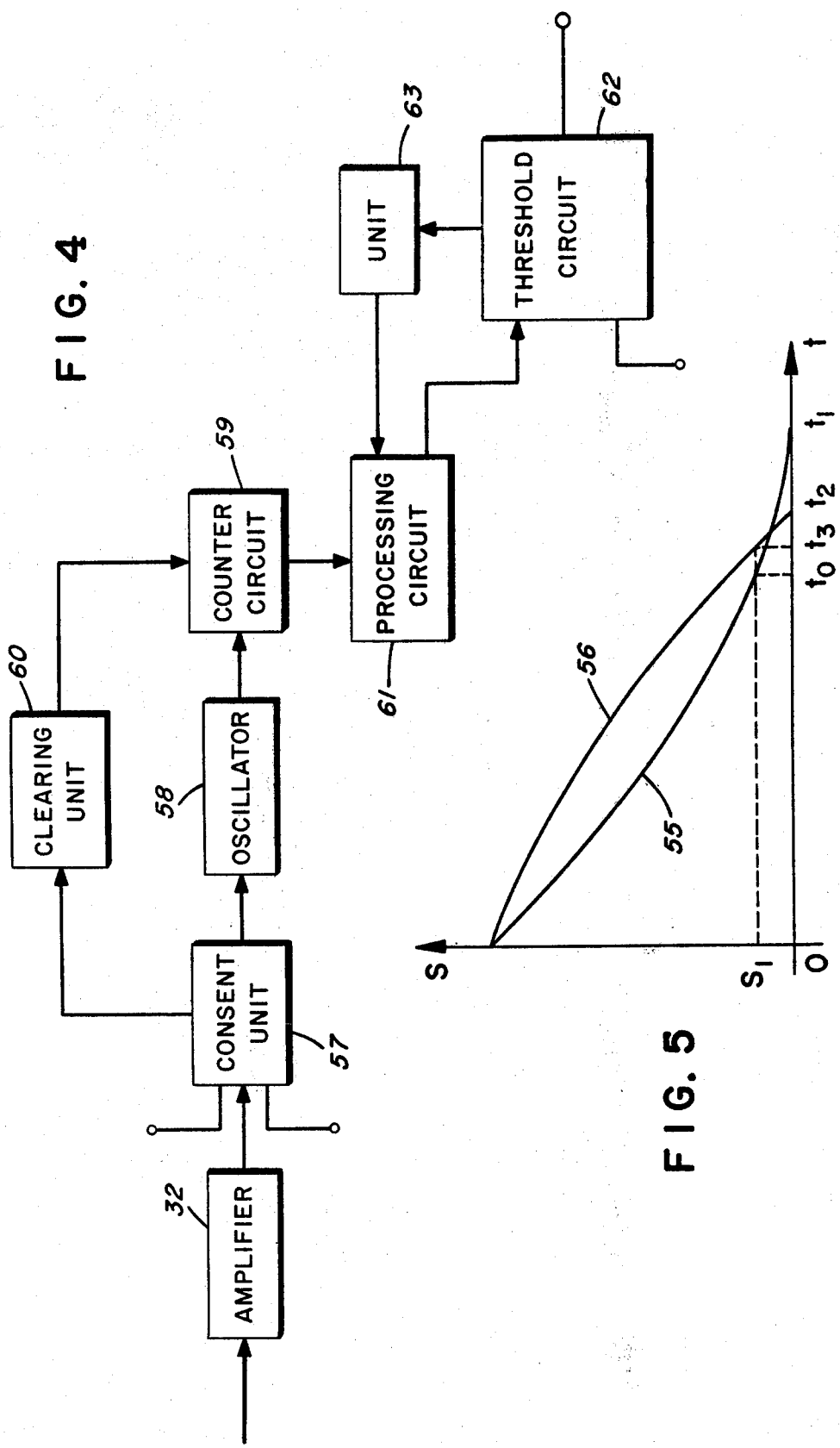

METHOD AND RELATIVE APPARATUS FOR CONTROLLING THE CUTTING CAPACITY OF THE GRINDING WHEEL OF A GRINDER

This is a division of application Ser. No. 365,734 filed May 31, 1973, now U.S. Pat. No. 3,895,526.

The present invention relates to an apparatus for checking the cutting capacity and operating dressing of the grinding wheel of a grinder, to optimize the production cycle of the machine itself.

This checking is generally carried out by periodically interrupting the machining cycle of the machine in accordance with a pre-set number of machined pieces.

By operating in such a way, it may happen, owing to the structure of the grinding wheel, to the material to be machined and to the different stock values of the pieces to be machined, that the wear rate of the grinding wheel is not necessarily always the same with the same number of machined pieces.

It may therefore happen that the grinding wheel is dressed when it is still efficient or that, in other cases, this operation is carried out with some delay, consequently affecting respectively the life of the grinding wheel and the accuracy of piece finishing.

This control method is substantially rather rough and uneconomical.

By other known methods dressing control is carried out based on the comparison between the real stock removal speed and an optimal advisably programmed speed. The dressing operation begins when in a certain piece the difference between the two values exceeds a pre-set maximum limit.

These methods, too, present however some disadvantages which limit their use, since the difference between the real and the programmed speed depends not only on the state of grinding wheel, but also on the initial stock of pieces, on possible defects of them and on the impact speed of the grinding wheel against the pieces at the beginning of the machining.

If the impact speed is considerable and even if the grinding wheel has a good cutting state, flexions suffered by the piece during machining are high, so that it goes through a strong recovery causing a considerable increase in the real removal speed.

In view of the aforementioned it may happen that the grinding wheel is dressed when it is still effective as a grinding wheel and need not be dressed.

The operation in this case is carried out independently of the state of the grinding wheel.

Therefore, with these known systems, too, it may happen that the grinding wheel is dressed when it is still efficient.

The technical problem that the present invention intends to solve is to provide a method and apparatus for checking the cutting capacity and for operating the dressing, which are reliable as required, with respect to operation timeliness, thus allowing the number of dressing operations to be reduced to the minimum, provided however, that a grinding wheel is always in such efficient condition as to produce perfectly machined pieces.

The problem is solved by a method in which the checking of the cutting capacity of the grinding wheel is carried out, according to the present invention, by determining for every piece, at the end part of the relative machining cycle, the value of at least one quantity responsive to the flexion state and the strains of the piece itself, by combining the succeeding so determined values and by comparing the value resulting from the combination with an experimentally obtained reference value.

In fact, it surprisingly has been noticed that at the end part of the working cycles, flexions and strains of pieces usually depend on the state of the grinding wheel, to a substantial degree.

Furthermore, to combine the data available for the different pieces avoids the hazard of interventions due to accidental or secondary factors.

An apparatus to realize the method comprises a device for detecting piece sizes during machining, consent means responsive to the device for detecting piece sizes, a processing group triggered at the end part of every machining cycle and fitted for calculating the value of at least one quantity responsive to the flexion state and the strains of pieces and for combining the succeeding calculated values, said processing group being connected to a threshold device for controlling the dressing of the grinding wheel.

The following description relates to preferential embodiments, given by way of a non-limiting example, with the help of the enclosed drawings, in which equal or equivalent parts present the same reference indexes and in which:

FIG. 4 represents a scheme in block form of an apparatus according to another embodiment of the invention; and FIG. 5 is a diagram illustrating the basic principles of the apparatus of FIG. 4.

Figure 1:
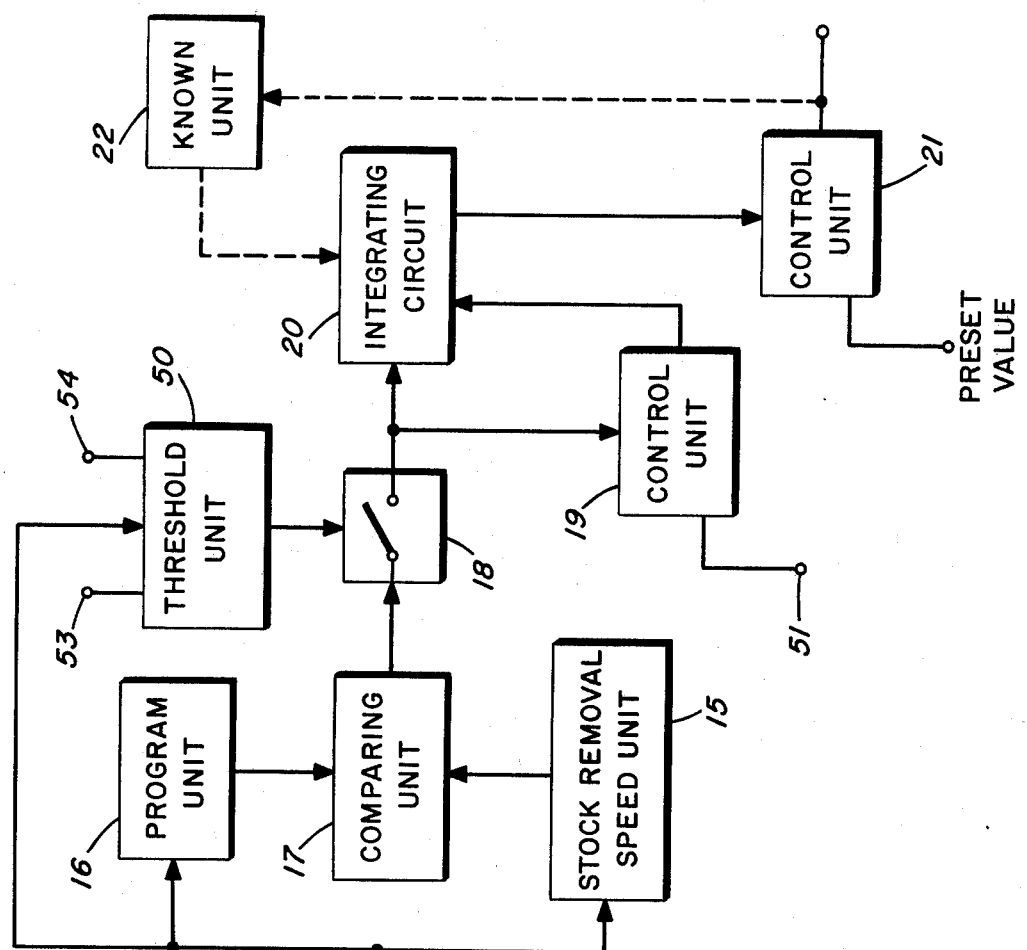
FIG. 1 represents a scheme in block form of an apparatus according to a first embodiment of the present invention.

With reference to FIG. 1, 11 represents a piece being machined, which is measured by a gauging head 12 fixed in any known way on a carriage 13 adapted for bringing the head to a measuring position.

The output signal of head 12 is sent to an amplifier 14 whose output is connected with a unit 15 capable of giving, at every instant, the real value of the stock removal speed.

The circuit forming unit may be the one disclosed in U.S. patent application Ser. No. 219,016 filed on Jan. 19, 1972, now U.S. Pat. No. 3,785,091.

Furthermore, the output of amplifier 14 is connected with a programming unit 16 fitted for giving, for every size value of the piece 11 being machined, a corresponding value of the feed speed of the wheelhead (not shown) carrying grinding wheel 52. The output signal of unit 16, i.e. the programmed feed speed of wheelhead, and the output signal of unit 15, i.e. the real stock removal speed for piece 11, are compared in a comparing unit 17, which carries out the difference between its two input signals.

The checking of the cutting capacity of the grinding wheel 52 is started when the stock of the machined piece reaches a certain value (it should be pointed out that such a value is closely related to the type of program).

To start checking at an excessive stock value (when the size of the piece 11 is considerably different from the standard size) is not convenient, since this checking would suffer too much from the initial machining conditions, which, owing to the transients caused by the impact of grinding wheel 52 on piece 11, are not sufficiently significant to obtain information about the opportunity of dressing grinding wheel 52.

On the contrary, at the end part of the machining cycle, flexions and strains on piece 11, following the initial machining conditions, are recovered to a large extent, by setting the programmed feed speed to the motor controlling wheelhead feed.

The remaining flexions and strains substantially depend on the cutting capacity of grinding wheel 52.

It is therefore clear that the difference between the real stock removal speed and the programmed speed at the end of the machining cycle depends mainly on the state of grinding wheel 52. In the apparatus of FIG. 1 the beginning of control is caused by a threshold unit 50, also connected to the output of amplifier 14 which closes switch 18 when the output signal of head 12 (and therefore stock) reaches, at the end of the machining cycle, a reference value properly set on terminal 53 of unit 50.

Threshold unit 50 is provided with another terminal 54, on which another reference value is set for causing the switching off of switch 18.

Switch 18, which is connected with comparison unit 17, is substantially closed when the stock of piece 11 varies between two pre-set values, the second of which may correspond, for example, to the moment the standard size of piece 11 is reached (stock equal to zero).

The closing time of switch 18 is therefore variable, according to the piece.

With the closing of switch 18, the difference signal at the output of unit 17, besides being introduced into an integrating circuit with memory 20, whose working will be further discussed in detail, is sent to a control unit 19 and compared with a reference signal.

This reference signal, introduced on a terminal 51, is chosen experimentally, on the basis of the values gauged at the output of unit 17 when the cutting capacity of the grinding wheel is considerable.

When the input signal of circuit 20 exceeds the reference signal present at terminal 51, unit 19 gives a consent signal and triggers integrating circuit 20, which integrates the signal present at its input for a time $\Delta t$ and stores the result of this integration. Besides being advisably sized, for the succeeding pieces 11 being machined, integrating circuit 20 adds up all integrals in the times $\Delta t$ of the signals with a width higher than the one of the reference signal at terminal 51.

The above-said can be analytically expressed by the following approximate formula:

$$U = \Sigma_1^n (V_A - V_p) \cdot \Delta t$$

in which:

$U$ represents the sum of voltage pulses (in volt per second) stored in integrating circuit 20;

$V_A$ a voltage proportional to the real stock removal speed;

$V_p$ a voltage proportional to the programmed speed;

$n$ the number of times $\Delta t$.

The output signal of circuit 20 is introduced into a control unit 21 and compared with a properly pre-set value.

Substantially, unit 21 is a threshold device. When the pre-set value is exceeded, unit 21 provides a control for dressing grinding wheel 52 and, at the same time, by means of a known unit 22, clears circuit 20.

By the control apparatus according to the present invention dressing can be performed when the cutting capacity of the grinding wheel is really insufficient, thus reducing idle working time to the minimum.

Figure 2:
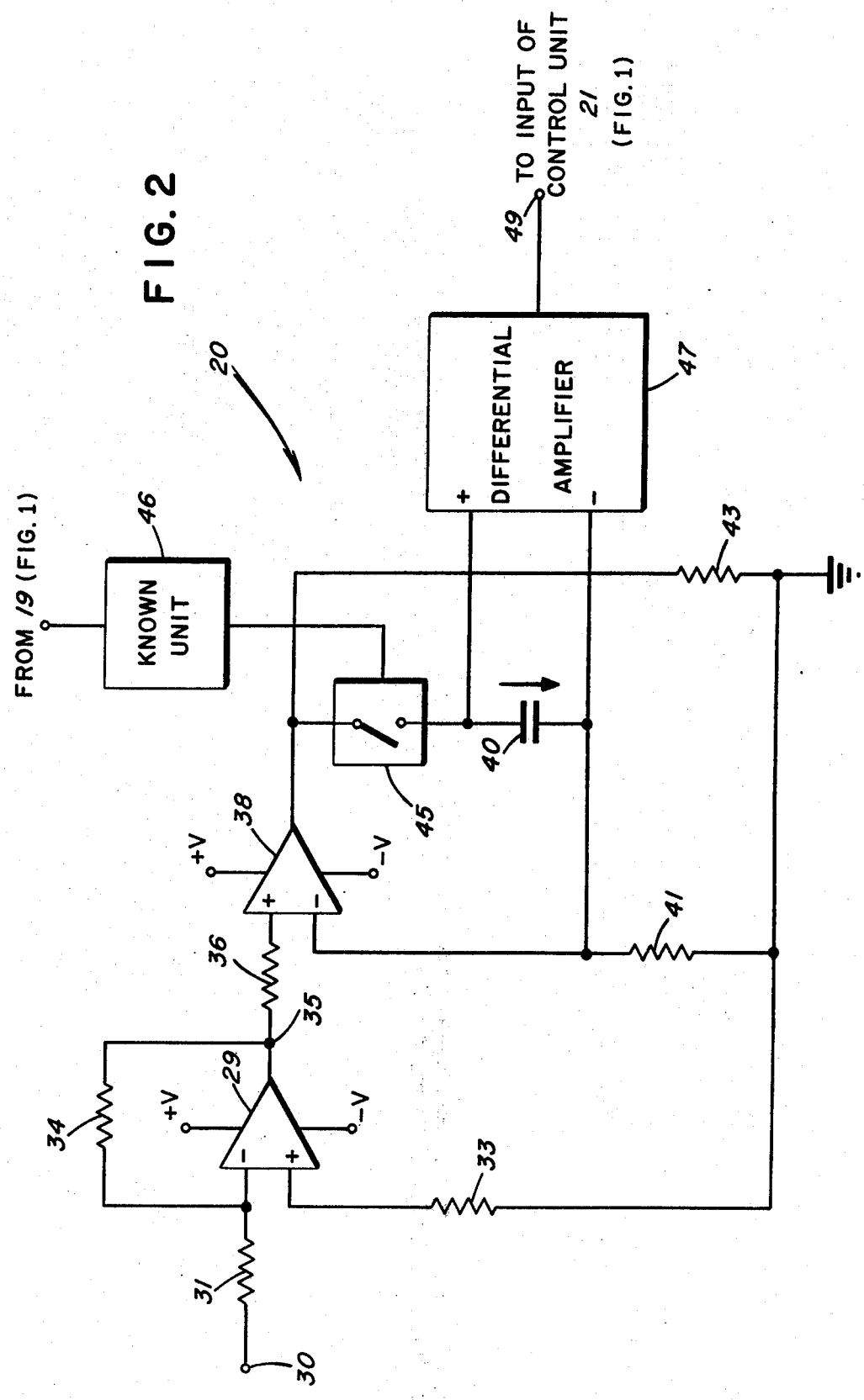

FIG. 2 shows a preferred embodiment of the integrating and memory circuit 20 of FIG. 1.

With reference to FIG. 2, from an input 30, through a resistor 31, a signal coming out of unit 17 reaches the negative input of an operational amplifier 29, i.e. the signal representing the difference between the real removal speed and the programmed speed.

Amplifier 29, whose positive input is earth-biased through a resistor 33, is fed by voltages +V and —V and is connected in negative feedback by a resistor 34 on its negative input. Amplifier 29, functioning as an inverter, gives on an output 35 a signal opposed in phase to the input signal.

The output signal of inverting circuit 29 is introduced, through a resistor 36, on the positive input of an operational amplifier 38, connected in negative feedback by a capacitor 40, when a switch 45 is closed, thus working as an integrating circuit. Amplifier 38 is fed by voltages +V and —V with its negative input being grounded by a resistor 41, and its output being grounded through a resistor 43.

Capacitor 40 is charged through switch 45, such charge depending on the value of resistor 41, which determines the value of the charging current of the capacitor itself.

Switch 45 is controlled by a known unit 46, which can open and close it.

Unit 46 is in connection (not shown in FIG. 2) with the output of unit 19 (FIG. 1).

Unit 4 is properly controlled in order to cause switch 45 to be closed when the input signal of circuit 20 (FIG. 1) exceeds the width of the reference signal set on terminal 51 of unit 19 (FIG. 1). When this is effected, voltage on capacitor 40 increases by a value proportional to the product of the width of the signal present at the output of amplifier 38 by closing time $\Delta t$ of switch 45.

When the signal at the input of integrator 20 of FIG. 1 has a width equal to or lower than the reference signal set on terminal 51 of circuit 19 (FIG. 1), the latter acts on unit 46 so as to cause the opening of switch 45. Under these conditions, the connection between the output of amplifier 38 and capacitor 40 being interrupted, the voltage at the ends of memory capacitor 40 undergoes no changes.

The voltage present at the ends of capacitor 40 is drawn and introduced to the inputs of differential amplifier 47 with a unitary gain and an input impedance sufficiently high so that discharge currents of capacitor 40 itself, when switch 45 is open, are scarcely appreciable.

Voltage on the output 49 of amplifier 47, corresponding to the sum of the signals memorized on capacitor 40 during intervals $\Delta t$, is introduced at the input of control unit 21, as explained above with reference to FIG. 1.

Figure 3:
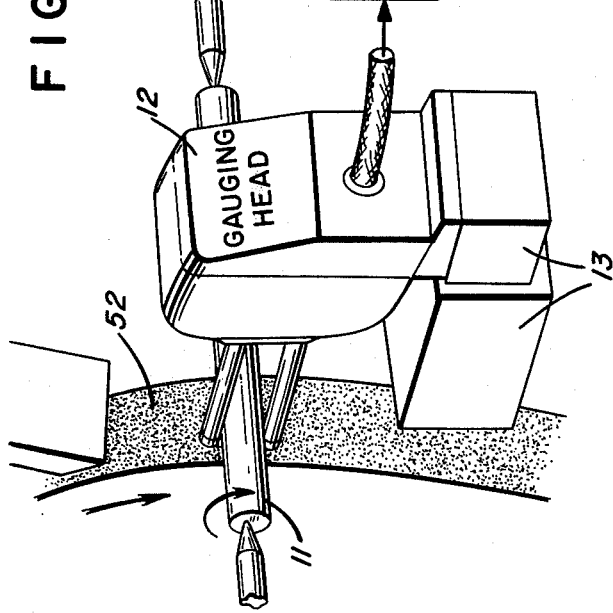
FIGS. 2 and 3 represent some of the devices of the apparatus illustrated in FIG. 1.
Figure 3:
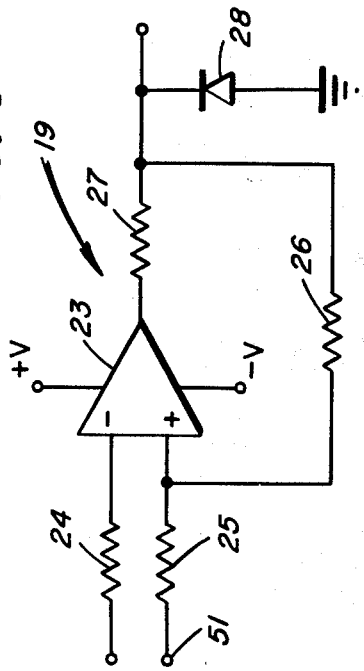

FIG. 3 represents a possible known scheme to realize control unit 19, which can obviously be considered as a threshold circuit.

The same scheme can be taken as a basis for realizing threshold devices 21 and 50.

With reference to FIG. 3, the signal present at the output of unit 17 (FIG. 1) is introduced to the negative input of an operational amplifier 23, through a resistor 24, and a reference signal, chosen advisably, as already explained, is introduced to the positive input of the same amplifier, through a resistor 25. Amplifier 23 is fed by voltages +V and −V and is connected in positive feedback by a resistor 26, at its positive input.

Resistor 27 limits current in the circuit, whereas diode 28, having the cathode connected with the output of amplifier 23 and the anode earth-biased, is used as a means for limiting output voltage of the amplifier itself.

Before checking the machining cycle, i.e. before closing switch 18 of FIG. 1, at the input of amplifier 23 only the reference signal is present, so that at the output of amplifier 23 there is a signal with a high voltage level which is able to turn off integrator 20 (FIG. 1).

During the checking of the machining cycle, i.e., after closing switch 18, if the signal representing the difference between the real stock removal speed and the programmed speed is lower than the above-named reference signal, integrator 20 remains off. If the difference signal exceeds the reference signal, the output of amplifier 23 is brought to a low voltage level, apt to trigger integrator 20 on.

Reopening of switch 18 can be controlled by means of a timer automatically activated at the closing of switch 18, instead of following the reaching of a certain stock value.

In such a way closing duration can be made constant for every piece 11, if required.

On the basis of another change of apparatus in FIG. 1, instead of making integrals of the quantity $V_A - V_p$ in time, for every piece 11 it is possible to store a value of $V_A - V_p$ (always determined in the last part of the machining cycle) and to add up the subsequent values, or their portions, till a pre-set limit is reached, in correspondence with which dressing is operated. Another variant to the control methods and apparatus described heretofore is illustrated with reference to FIGS. 4 and 5.

According to this variant, the checking of the cutting capacity of grinding wheel 52 is effected by determining the duration of one or more end phases of the machining cycle.

It is known that the passage from one phase to another, for instance from a finishing phase of piece 11 to a spark-out phase (machining with no feed of wheelhead) in many grinders is automatically controlled at the reaching of pre-set stock values.

If the cutting capacity of grinding wheel 52 is limited the grinding wheel itself removes little stock in the initial part of the cycle. However, it bends and stresses piece 11 very much. In the end part of the cycle, piece recovery brings about a removal higher than the one obtained by an efficient grinding wheel. Therefore the relative machining phases turn out to be shorter.

With reference to FIG. 5, $S_1$ is the value of stock in correspondence with which there begins the last machining phase, which ends at the reaching of standard size (stock equal to zero).

Curve 55 represents the changes of stock S in time $t$ for piece 11 machined by grinding wheel 52 having a good cutting capacity.

Curve 56 represents the changes of S in time $t$ for a similar piece, machined, however, by a grinding wheel with a poor cutting capacity.

The duration of the last machining phase in the case of curve 55 is given by:

$$T_1 = t_1 - t_o,$$

in the case of curve 56 by: $T_2 = t_2 - t_3$.

It results:
$$T_2 < T_1.$$

According to the present invention, the checking of cutting capacity of grinding wheel 52 is effected by calculating, for every piece 11 towards the end of the machining cycle, the value of function:

$$f = (\frac{1}{T} - K)$$

in which T is the duration of a pre-set machining step, or more generally, the time it takes to remove a pre-set stock $S_1 - S$; K is a constant, experimentally chosen, which considers the duration of the phase when the grinding wheel is efficient.

Then the sum:

$$\Sigma (\frac{1}{T} - K)$$

is done, and, at the reaching of an experimentally pre-set limit, dressing is controlled.

The scheme in block form of FIG. 4 shows an apparatus to accomplish the method according to the aforementioned variant.

Amplifier 32 is connected with a consent unit 57 which fires an oscillator 58 and makes it oscillate when the voltage provided by amplifier 32 is comprised between two pre-set values.

A counter circuit 59 calculates the number of oscillations, thus indicating the interval of time T during which the oscillator is fired.

At the end of every calculation, counter 59 is set to zero by a clearing unit 60.

The succeeding calculations of counter 59 are brought to the input of a processing circuit 61 which calculates function $$\Sigma (\frac{1}{T} - K).$$

When the signal coming out of processing circuit 61 exceeds a pre-set reference value, experimentally determined, a threshold circuit 62 controls dressing and clears processing circuit 61, through a unit 63.

Obviously, the above-described embodiments can undergo other changes and variants equivalent from a structural and functional viewpoint without falling outside the scope of the present invention.

What is claimed is:

1. Apparatus for checking the cutting capacity and controlling the dressing of the grinding wheel of a grinding machine, the machine including machining control means for controlling its operation cycles, comprising:

measuring means for providing a measuring signal responsive to the size of the workpieces being machined;

processing means for calculating at least one quantity responsive to the cutting capacity of the grinding wheel, said processing means including:

first circuit means connected to the measuring means for receiving said measuring signal and for processing the same to generate a signal depending on the speed of stock removal;

second circuit means connected to the first circuit means for generating a combined signal depending on subsequent values of the signal generated by the first circuit means; and third circuit means connected to the measuring means and to at least one of said first and second circuit means for triggering the latter in determined phases of the operation cycles to make said combined signal indicative of the cutting capacity of the grinding wheel to provide said quantity; and dressing control means connected to the third circuit means for generating a dressing control signal when said combined signal exceeds a preset value.

2. The apparatus according to claim 1, in which said machining control means includes a program unit connected to said measuring means for providing a control signal to set, on the basis of the measured piece sizes, the values of the feed speed of the grinding wheel, wherein said first circuit means includes a first electric unit adapted to generate a signal indicative of the stock removal speed and a second electric unit to compare said signal indicative of the stock removal speed with said control signal for providing a difference signal; and said second circuit means includes an integrating and memory circuit for integrating and storing said difference signal for every piece being machined and to add up the resulting values of the succeeding integrations.

3. The apparatus according to claim 2, wherein said third circuit means includes switch means connected to said second electric unit and said integrating and memory circuit, said switch means being adapted to connect the integrating and memory circuit with said second electric unit when said measuring signal reaches a pre-set value.

4. The apparatus according to claim 3, wherein said third circuit means includes a further switch means connected to said switch means and said integrating and memory circuit for triggering the latter when said difference signal exceeds a determined value.

5. The apparatus according to claim 1, in which said third circuit means includes a control circuit connected to the measuring means and the first circuit means, for triggering the second circuit means when said measuring signal reaches a pre-set value, the first circuit means including an electric unit adapted to calculate the time necessary to remove a preset amount of stock, to provide said signal depending on the speed of stock removal.

6. Apparatus for checking the cutting capacity and controlling the dressing of the grinding wheel of a grinding machine, the machine including program means generating a control signal to set the speed of the grinding wheel feed depending on the actual size of the workpiece being machined, comprising:

a gauging device for providing a measuring signal indicative of the size of the workpiece being machined; an electric unit connected to the gauging device to receive said measuring signal, the electric unit being adapted to generate an output signal indicative of the speed of stock removal;

a comparing unit connected to the electric unit and the program means for providing a difference output signal resulting from the comparison between the control signal and the signal indicative of the speed of stock removal;

an integrating circuit adapted to receive at its input said difference output signal for providing an output signal resulting from integrations of the input difference signal;

switch means arranged between said comparing unit and said integrating circuit for permitting the latter to receive said difference output signal, the switch means including a control terminal connected to the gauging device, the control terminal being adapted to control the switching on of the switch means when the workpiece size reaches a determined value;

a triggering unit connected to the switch means and the integrating circuit for triggering the latter when said difference output signal exceeds a determined value; and dressing control means connected to the integrating circuit for generating a dressing control signal when the output signal of the integrating circuit exceeds a pre-established value.

7. Apparatus for checking the cutting capacity and controlling the dressing of the grinding wheel of a grinding machine, the machine including machining control means for controlling the different phases of machining depending on the size of the workpiece being machined, comprising:

a gauge adapted to provide a measuring signal responsive to the size of the workpiece being machined; a firing circuit connected to the gauge for providing a firing signal when the measuring signal is comprised between two preset values;

a time calculating circuit connected to the firing circuit for receiving the firing signal and calculating the time intervals intercurring between the occurrence, for the subsequent workpieces, of said preset values of the measuring signal;

a processing circuit connected to the time calculating circuit for generating subsequent signals depending on the subsequent values of said time intervals and for generating a combination signal of said subsequent signals; and a dressing control circuit connected to the processing circuit for providing a dressing control signal when said combination signal exceeds a determined value.

* * * * *